(12) United States Patent
Richardson et al.

(10) Patent No.: US 6,307,100 B1
(45) Date of Patent: Oct. 23, 2001

(54) CATALYTIC OXIDATION OF HYDROCARBONS

(75) Inventors: David Richardson, Gainesville, FL (US); Cheng Xu, Lawrenceville, NJ (US); Khalil Abboud; Garry K. Weakley, both of Gainesville, FL (US)

(73) Assignee: University of Florida Research Foundation

( * ) Notice: Subject to any disclaimer, the term of this patent is extended or adjusted under 35 U.S.C. 154(b) by 0 days.

(21) Appl. No.: 09/642,496

(22) Filed: Aug. 18, 2000

Related U.S. Application Data

(63) Continuation-in-part of application No. 09/506,053, filed on Feb. 17, 2000.
(60) Provisional application No. 60/152,499, filed on Sep. 2, 1999, and provisional application No. 60/120,473, filed on Feb. 17, 1999.

(51) Int. Cl.$^7$ ............................ C07C 51/31; C07C 55/14; B01J 31/00; B01J 37/00; C07B 33/00
(52) U.S. Cl. ............................................. 562/543; 502/155
(58) Field of Search ............................... 562/543; 502/155

(56) References Cited

U.S. PATENT DOCUMENTS 4,900,871 * 2/1990 Ellis, Jr. et al. ...................... 568/399

* cited by examiner

Primary Examiner—Charanjit S. Aulakh
(74) Attorney, Agent, or Firm—Akerman Senterfitt

(57) ABSTRACT

Disclosed are catalysts useful for catalyzing the synthesis of adipic acid from cyclohexane and oxygen. Also disclosed are methods of making the catalysts, methods of using the catalysts to catalyze the production of adipic acid from cyclohexane and oxygen, and kits containing the catalysts.

47 Claims, No Drawings

CATALYTIC OXIDATION OF HYDROCARBONS

CROSS-REFERENCE TO RELATED APPLICATIONS

The present application is a continuation-in-part of U.S. patent application Ser. No. 09/506,053 filed Feb. 17, 2000, which claims the benefit of U.S. provisional patent applications Ser. Nos. 60/120,473 and 60/152,499 filed Feb. 17, 1999 and Sep. 2, 1999, respectively. All are incorporated herein by reference.

FIELD OF THE INVENTION

This invention relates to production of chemical products via the catalytic oxidation of a hydrocarbon.

BACKGROUND OF THE INVENTION

Adipic acid (AA) is a raw material used in the production of many different materials including organic polymers (most notably Nylon-6,6), fibers, plasticizers, and food additives. The manufacture of these materials requires millions of tons of highly pure adipic acid each year.

Several methods of producing adipic acid are known. The currently predominant industrial process is performed in two separate steps. The first step is oxidizing cyclohexane to a mixture of cyclohexanone and cyclohexanol (KA mixture), and the second step is converting the KA mixture to adipic acid. The second step is typically performed using concentrated nitric acid (~55 wt % in the reaction) as an oxidant. Unfortunately, the nitric acid oxidation step results in the production of $NO_x$ (especially $N_2O$) byproducts that can pollute the atmosphere and are not readily recyclable.

One step processes for preparing adipic acid by air or peroxide oxidation of cyclohexane have been reported. See, e.g., U.S. Pat. Nos. 5,221,800; 5,929,277; and Catalysis Today, 9: 237, 1991. These processes are typically performed using a Co(III) catalyst at high oxygen pressure (e.g., 20–30 atn) or N-hiydroxy- phthalimide/Co/Mn catalysts at low $O_2$ pressure (Iwahama, T.; Syojyo, K.; Sakaguchi, S.; Ishii, Y. Organic Proc. Res. Devel. 1998, 2, 255–260). Despite the potential efficiencies and cost savings associated with such one step processes, the two step process continues to be preferred in the industry because conventional one step processes have not been optimized for large scale syntheses. For example, conventional one step processes using a Co-based catalyst require that a very high concentration (e.g., about 0.01 M) of the catalyst be included in the reaction mixture. As this catalyst is relatively expensive, cost considerations mandate that it be recycled using an extraction procedure prior to reuse in additional runs. Conventional one step processes also offer relatively low selectivity, and result in an adipic acid product of relatively low purity (e.g., less than about 70% pure). For these reasons. cobalt-catalyzed one step oxidation processes generally involve costly purification/recycling steps for purifying the adipic acid from by-products of the reaction, and for recycling the catalyst.

SUMMARY

A chemical process has been developed for the catalytic, single step conversion of cyclohexane to solid adipic acid by air oxidation. A composition that catalyzes this process includes an transition metal such as iron or ruthenium in complex with a pyridyl ligand such as pyridine; 4,4'-diphenyl-2,2'-bipyridine (dpbp); 1,10 phenanthroliine (phen); 4,7-diphenyl-1,10-phenantlhroline (dpphen); or 2,9-dimethyl-4,7-diphenyl-1,10-phenanthroline (dmdpphen). This composition can be readily dissolved in numerous cyclohexane/ cosolvent mixtures, permitting a reaction mixture comprising the catalytic composition, cyclohexane, and cosolvent to be in a homogeneous state (i.e., all components dissolved together in a liquid phase) at the initiation of the reaction. The reaction can be run under moderate temperatures and moderate pressures of air or other oxygen source to yield solid adipic acid precipitates from the reaction mixture solution upon cooling. Even unrecrystallized, the solid adipic acid precipitates can be greater than 95% pure (i.e., contaminated with less than 5% other substances). The solid adipic acid can then be filtered out of the reaction mixture, leaving behind a filtrate that can then be reused to produce additional adipic acid. Thus, the process is amenable to a continuous synthetic process whereby, for example, formed solid adipic acid can be removed from the reaction mixture as it is produced by repetitively cooling and then filtering different aliquots of the reaction mixture, and then returning the liquid filtrate to the reaction vessel where it is further reacted to produce additional adipic acid.

The invention thus offers several advantages over conventional two step and reported one step techniques. For example, compared to the conventional two step process, the invention allows relatively easier and less expensive isolation and purification of the adipic acid as the one step process can be performed at moderate temperatures and pressures to yield solid precipitates containing greater than about 95% pure adipic acid . The invention also avoids the use of the highly corrosive acidic solvents (e.g., nitric acid) used in conventional two step adipic acid syntheses, and therefore does not generate polluting nitrogen oxides. These advantages should decrease the costs associated with adipic acid production by reducing the complexity of plant design and maintenance (e.g., single step process vs. two step process), lowering energy costs due to ease of purification (e.g., higher purity solid recovered directly), reducing pollution (e.g., no $NO_x$ byproducts to recover), lowering raw material costs (e.g., air vs. nitric acid), and lowering new plant construction costs (e.g., noncorrosive conditions).

The invention also offers a marked improvement over conventional one step processes in that fewer or simpler purification/recycling steps are required to produce highly pure adipic acid in a cost efficient manner. For example, unlike conventional one step processes, the invention does not require a complex catalyst recovery procedure. Rather, recycling of the catalyst in the present invention presents much less of a problem because the catalysts within the invention are relatively inexpensive, are not required in high concentrations, and can be reused without being repurified.

Accordingly the invention features a catalyst for catalyzing the synthesis of a chemical product from a hydrocarbon and oxygen. In a preferred variation, the chemical product is adipic acid and the hydrocarbon is cyclohexane. The catalyst is made up of a transition element such as iron or ruthenium complexed with a polypyridyl ligand such as pyridine, dpbp, phen, dpphen, or dmdpphen. The transition element can be complexed with a counter ion such as $ClO_4-$, $Cl^-$, $(CH_3)_3CCO_2^-$, or $CF_3SO_3^-$. Preferred catalysts of have between one and twelve mole equivalents of the pyridyl ligand per mole equivalent of the transition element.

Various catalysts within the invention can catalyze the production of adipic acid from cyclohexane in a single step process at a low concentration such as about 0.00002 to about 0.002 moles of the catalyst per mole of cyclohexane. In many cases, the catalysis occurs without nitrogen oxide production. Preferred catalysts within the invention have the ability to catalyze the production of a solid product from cyclohexane and oxygen in a single reaction vessel. The solid product being greater than about 70% or in some case greater than about 95% pure adipic acid.

In another aspect, the invention features a method of making a catalyst for the synthesis a chemical product from a hydrocarbon and oxygen. This method includes the steps of: (A) providing a transition element, a pyridyl compound, and a reaction mixture including the hydrocarbon; (B) adding the transition element and the pyridyl compound to the reaction mixture; and (C) placing the reaction mixture under conditions which cause the transition element and pyridyl compound to be able to function together as a catalyst for the synthesis of the chemical product from a hydrocarbon and oxygen. In variations of this method, the chemical product is adipic acid and the hydrocarbon is cyclohexane.

Other methods of making a catalyst for catalyzing the synthesis of adipic acid from cyclohexane and oxygen are also included in the invention. For example, preferred versions of such methods include the steps of: (A) mixing together a composition including a pyridyl compound and a composition including a transition element to form a reaction mixture; (B) allowing the reaction mixture to react under conditions which result in the formation of a solid material containing the catalyst; and (C) purifying the solid material from the reaction mixture. In variations of these methods, the pyridyl compound is pyridine, dpbp, phen, dpphen, or dmdpphen, and the transition element is iron or ruthenium.

The invention also features a method of catalyzing the synthesis of a chemical from a hydrocarbon and oxygen. This method includes the steps of: (A) providing a catalyst including a transition element and a pyridyl compound; (B) mixing the catalyst with the hydrocarbon and an oxygen source to form a reaction mixture; and (C) placing the reaction mixture under conditions that result in the production of the chemical in the reaction mixture. In a preferred variation of this method, the chemical can be adipic acid and the hydrocarbon can be cyclohexane.

The step of placing the reaction mixture under conditions that result in the production of the chemical in the reaction mixture can include placing the reaction mixture into a reaction vessel, adjusting the temperature of the reaction mixture to between about 100–150° C., cooling the reaction mixture until a solid precipitate forms in the reaction mixture after the step of adjusting the temperature of the reaction mixture to between about 100–150° C., and/or adjusting the pressure of the oxygen source in the reaction vessel such that the partial pressure of oxygen in the reaction vessel is between about 200 and 3500 kPa (e.g., 750 kPa). In some cases, it is preferred to add an aprotic, polar, aromatic co-solvent such as ortho-dichlorobenzene to the reaction mixture to facilitate the reaction. In other cases, it is preferred not to add any co-solvent to the reaction mixture.

Using this method, adipic acid can be produced as a solid precipitate in the reaction mixture. The solid precipitate can be separated from the reaction mixture to yield (a) isolated adipic acid and (b) a partially reacted reaction mixture. The partially reacted reaction mixture can be placed into a reaction container and further reacted under conditions that result in the production of additional adipic acid. Additional cyclohexane and oxygen can be added to a vessel containing the partially reacted reaction mixture to replenish these reactants, and enhance the yield of product.

Also within the invention is a kit for catalyzing the synthesis of adipic acid from cyclohexane and oxygen. The kit can include a catalyst of the invention and written instructions for using the catalyst to catalyze the synthesis of adipic acid from cyclohexane and oxygen.

In yet another aspect, the invention features a reaction mixture containing a hydrocarbon, oxygen, and a catalyst for catalyzing the synthesis of a chemical product from the hydrocarbon and the oxygen. The catalyst of the kit can be a transition element such as iron or ruthenium complexed with a pyridyl ligand.

As used herein, the term "catalyze" means to directly or indirectly cause an increase in the rate of a chemical reaction. A composition "catalyzes" a reaction when the reaction rate increases after the composition is included in the reaction, regardless of whether the composition itself is catalytically active or is converted into a catalytically active species during the reaction. Similarly, the term "catalyst" means a substance that causes in increase in the rate of a chemical reaction when included in that reaction. The term catalyst thus includes the actual substance added to the reaction (which itself may not be catalytically active), as well as any catalytically active derivatives of the substance formed in the reaction.

As used herein, when referring to a chemical reaction, the phrase "singing step process" means that the reaction can be completed in a single reaction vessel without acquiring the removal or addition of reagents after the initiation of the reaction.

By the phrase "complexed with" or "in complex with" means physically associated with, e.g., by a covalent bond, an ionic bond, a coordinate complex, Van der Waals forces, hydrogen bonds, etc. Thus, for example, a transitional element is complexed with a pyridyl ligand if one or more atoms of the transitional element are physically associated (e.g., via a coordinate covalent bond) with one or more ligands having a pyridyl group.

By reference to the elements "iron," "ruthenium," or other transition elements is meant any state of the element including non-ionic and ionic forms, as well as all oxidation states.

Unless otherwise defined, all technical terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

Other features and advantages of the invention will be apparent from the following detailed description, and from the claims.

DETAILED DESCRIPTION

The invention is based on the discovery of new methods and compositions for catalyzing the oxidation of hydrocarbons to form chemical products. A preferred reaction of the invention is the oxidation of cyclohexane to solid adipic acid. One process for the oxidation of cyclohexane is illustrated with the following chemical equation:

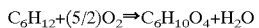

$$C_6H_{12} + (5/2)O_2 \rightarrow C_6H_{10}O_4 + H_2O$$

In this reaction, in the presence of oxygen ($O_2$), the hydrocarbon (cyclohexane) is converted into the chemical product (adipic acid) and water. Other known processes for oxidizing hydrocarbons might also be used in the invention as described below or by making simple alterations to the preferred embodiments described herein.

This oxidation of cyclohexane can be catalyzed using a transition metal complexed with a pyridyl ligand. Because such catalysts are soluble in either neat cyclohexane or various cyclohexane/cosolvent mixtures, their use allows a reaction mixture comprising the catalytic composition, cyclohexane, and cosolvent (if included) to be in a homogeneous state (i.e., all components dissolved together in a liquid phase) at the initiation of the reaction. Addition of oxygen and heat to the homogeneous reaction mixture results in oxidation of the cyclohexane. Subsequently cooling the reaction mixture effects precipitation of a solid which is typically >95% pure adipic acid. The solid adipic acid can be isolated from the reaction mixture, and the remaining liquid phase reused to produce additional adipic acid. Thus, this preferred process is especially amenable to a continuous synthetic process whereby, for example, formed solid adipic acid is continually removed from the reaction mixture, while the remaining liquid portion of the reaction mixture is further reacted to produce additional adipic acid. While the foregoing describes one particularly preferred version of the invention, many other methods and compositions are also within the invention. Some of these are described below in further detail.

Materials

Preferred compositions featured in the invention are those that catalyze the synthesis of a chemical product from a hydrocarbon and oxygen.

Chemical Products

Chemical products within the invention include any that can be made by oxidizing a hydrocarbon using a catalyst of the invention. The preferred chemical product synthesized using the methods and compositions of the invention is adipic acid. Nonetheless, as synthetic reactions similar to the oxidation of cyclohexane are known in the art, it is envisioned that other chemical products could also be synthesized using the invention. See, e.g., Kirk-Othmer Encyclopedia of Chemical Technology ($3^{rd}$ and $4^{th}$ editions). In particular, chemical products having the general formula of $C_xH_yO_z$ (where x, y, and z are integers) such as alcohols, ketones, aldehydes, carboxylic acids, esters, enols, and epoxides might be made by adapting the catalysts and methods of the invention to conventional reactions for producing such chemicals. The processes of the invention are advantageous in that they can yield highly pure chemical products. For example, for the oxidation of cyclohexane to adipic acid using a transition element complexed with a pyridyl ligand, adipic acid can be produced in a form greater than about 70% pure (e.g., 71%, 72% 73%, 74%, 75%, 80%, 85%, 90%, 95%, 99%, etc.) without recrystallization or repurification steps.

Hydrocarbons

A hydrocarbon is any molecule comprising at least one hydrogen atom bonded to at least one carbon atom. Hydrocarbons useful in the invention include those that can serve as a reactant that can be oxidized to form a chemical product. Hydrocarbons may have any number of carbon atoms per molecule (e.g., 1, 2, 3, 4, 5, 6, 7, 8, 9, 10, 11, 12, 13, 14, 15, 20, 30 or more carbon atoms per molecule). Examples of hydrocarbons include alkanes (e.g., methane, ethane, propane, butane, pentane, hexane, heptane, octane, nonane, decane, undecane, dodecane, etc.), cycloalkanes (e.g., cyclopentane, cyclohexane, etc.), alkenes (e.g., propene, butene, pentene, hexene, etc.), alkynes (e.g., acetylene), aromatic hydrocarbons (e.g., benzene, napthalene, etc.), and mixtures of the foregoing (e.g., petroleum and petroleum derivatives).

Those that are efficiently oxidized in the presence of a catalyst comprising a transition element and a pyridyl ligand are preferred. Examples of hydrocarbons thought to be particularly useful in this aspect of the invention include cyclohexane, hexane, cyclooctane, and adamantane. Depending on the particular synthetic reaction involved, different hydrocarbons, or even mixtures of different types of hydrocarbons will be preferred.

For the synthesis of adipic acid, cyclohexane is preferred as it is efficiently oxidized to adipic acid in the presence of various catalysts within the invention. Cyclohexane typically is a petroleum derivative and can be readily obtained from several sources. Other hydrocarbons for use in the invention arc also readily available from several sources (e.g., Sigma-Aldrich, St. Louis, Mo.).

Oxygen Sources

Although the form of oxygen during the oxidization process is not limited to gaseous dioxygen ($O_2$), this form is presently preferred because it is readily available, relatively inexpensive, stable, and effective in the reactions of the invention. The invention is also not limited as to the source of the dioxygen. Dioxygen can be delivered, for example, as a 100% pure gas or liquid, or as a mixture of dioxygen and one or more other substances. One suitable source of dioxygen that is particularly preferred is gaseous air, as air is typically safer to use than other mixtures containing higher concentrations of dioxygen or 100% pure dioxygen, and is also among the least inexpensive and most available sources.

Catalysts

The process of oxidizing the hydrocarbon according to the invention is facilitated using a catalyst as many hydrocarbons are difficult to oxidize without the use of a catalyst. The preferred catalyst is a combination of a transition element in complex with an organic ligand, where the combination can be added to and preferably dissolved in a reaction mixture containing a hydrocarbon to catalyze the oxidation of the hydrocarbon within the reaction mixture.

Many types of transition elements can be used with this process. Examples of transition elements include ruthenium (Ru), iron (Fe), osmium (Os), cobalt (Co), iridium (Ir), manganese (Mn), rhenium (Re), rhodium (rh), nickel (Ni), lead (Pb), and platinum (Pt). Ionic forms of the foregoing are preferred. For example, ionic forms with oxidation states of between +2 to +7 are preferred in many cases such as those where free radical intermediates facilitate radical chain reaction-mediated catalytic events. More specifically, preferred ionic forms include: Fe(II), Fe(III), Co(II), Co(III), Ni(II), Ni(III), Ru(II), Ru(III), Rh(III), Pb(II), Pb(IV), Os(III), Os(IV), Ir(III), Ir(IV), Pt(II), Pt(IV), Mn(II), Mn(III), Mn(IV), Mn(VII), Re(IV), Re(VI), and Re (VII). For the oxidation of cyclohexane to adipic acid, presently preferred transition elements to be complexed with the organic ligand are iron(II), iron(III), and ruthenium(II) as these have been shown to efficiently catalyze this synthetic reaction. For ease of handling and dissolution, ionic forms of transition elements can also be used as salts, i.e., complexed with one or more counter ions such as $ClO_4^-$ (perchlorate), $Cl^-$ (chloride), $(CH_3)_3CCO_2^-$ (trimethylacetate or tma) and $CF_3SO_3^-$ (Trf, Otf, or tiiflate), and other anionic groups.

Any organic ligand compatible with the selected transition clement and suitable for use as a catalyst in the selected reaction can be used in the invention. Preferred organic ligands include those that (1) can complex with (e.g., chelate) the particular transition element selected, (2) help solubilize the transition element in the reaction mixture, and (3) cooperate (e.g., interact) with the transition element to efficiently catalyze the desired chemical synthesis. Organic ligands having one or more pyridine groups and/or one or more imine groups generally posses such qualities for many reactions within the invention. For example, Schiffbases, poirphyrin and pyridyl ligands can be used as the organic ligand. Presently, pyridyl ligands such as phenanthrolines, pyridine, bipyridines, terpyridines, tetrapyridines, etc. are generally preferred, but others may be more preferred depending on the particular chemical reaction involved.

For the conversion of cyclohexane to adipic acid, the presently preferred ligands are pyridine, dpbp, phen, dpphen, and dmdpphen. These ligands are particularly preferred because they can effectively complex with preferred transition elements iron and ruthenium to catalyze the production of adipic acid from cyclohexane. Presently preferred catalysts are thus Fe(II) complexed with dpphen or dmdpphen; Fe(III) complexed with phen, dpphen, or pyridine; and Ru(II) complexed with dmdpphen.

Any ratio of organic ligand to transition element that catalyzes the oxidation of a hydrocarbon to a chemical product can be used. Particular ratios that are preferred are expected to vary depending upon the transition element and organic ligand selected, as well as the particular reaction involved, addition of cosolvents or other extraneous materials, temperature, pressure, or other reaction conditions. For each particular organic ligand-transition element complex, preferred ratios can be determined by simply adding different ratios of each to the reaction mixture (or method of synthesizing the catalyst) and analyzing which are the most efficient catalysts under the selected reaction conditions.

For example, for the one step air oxidation of cyclohexane to adipic acid at about 130° C. with about 550 kPa partial pressure of $O_2$, using Fe(II), Fe(III), or Ru(II) complexed with pyridine, dpbp, phen, dpphen or dmdpphen, a preferred ratio is about one to twelve (e.g., 1, 1.5, 2, 2.5, 3, 3.5, 4, 4.5, 5, 5.5, 6, 7, 8, 9, 10, 11, and 12) mole equivalents of pyridyl ligand per mole equivalent of transition element.

Cosolvents

Other than the hydrocarbon reactant itself, one or more other solvents (i.e., cosolvents) can be added to the reaction mixture to help dissolve the reactants and catalyst of the reaction mixture into a homogeneous state (e.g., hydrocarbon and catalyst dissolved together in a liquid phase). Those solvents capable of both dissolving the constituents of the process and not hindering the reaction are acceptable for use with the invention. Typically, the choice of the solvent for use as a cosolvent depends upon the particular constituents used, as, for example, one particular solvent may be capable of dissolving one set of constituents but not another. As such, many types of solvents can be used with this process. Examples of solvents that might be used include acetic acid, acetonitrile, benzene, and methylacetate.

For the oxidation of cyclohexane into adipic acid using an Fe(II)-dpphen, Fe(II)-dmdpphen, and/or Ru(II)-dmdpphen catalyst, the preferred solvent is an aprotic, polar aromatic solvent that dissolves both the foregoing catalysts and cyclohexane. Specifically, ortho-dichlorobenzenie is the presently preferred cosolvent for the above synthetic reaction as both the Fe(II) and Ru(II) catalysts have high solubility in the solution combination of ortho-dichlorobenzene and cyclohexane. Ortho-dichlorobenzene also has the preferred property of being inert towards oxidization and thus not being chemically altered by oxidization. In other cases, for the oxidation of cyclohexane no co-solvent is added, e.g., using $Fe(dpphen)_3(Trf)_2$ or $Fe(tma)_2$ plus dpphen as catalyst.

Methods for Making Catalysts

Catalysts within the invention can be prepared by any known method for complexing an organic ligand with a transition clement. For example, catalysts within the invention can first be prepared as a solid and then added to the reaction mixture. Alternatively, catalysts can be prepared in situ (i.e., within the reaction mixture itself) by separately adding the transition element and the organic ligand to the reaction mixture. For either technique, the actual catalytically active species may take the form of the starting form of the transition element (i.e., the form prior to initiation of the reaction) in complex with the starting form of the organic ligand. But, for many reactions, the catalytically active species probably takes the form of a degradation or reaction product formed from the transition element and/or the organic ligand during the reaction. Thus, both the starting form of the transition element complexed with the starting form of the organic ligand, and other forms of the foregoing created during the reaction are within the invention.

A preferred method of making a catalyst for the synthesis a chemical product from a hydrocarbon and oxygen includes the steps of: (A) providing a transition element, a organic ligand (e.g., a pyridyl compound), and a reaction mixture comprising the hydrocarbon; (B) adding the transition element and the organic ligand to the reaction mixture; and (C) placing the reaction mixture under conditions which cause the transition element and organic ligand to be able to function together as a catalyst for the synthesis the chemical product from a hydrocarbon and oxygen.

The foregoing method can be achieved by adapting standard techniques in synthetic chemistry. For example, one method of preparing a catalyst in situ is to add separately both a salt of the transition element and the organic ligand to the reaction mixture under conditions where the an ionic form of the transition element (formed upon dissolution of the salt in the reaction mixture) complexes with the organic ligand within the reaction mixture. For instance, to make a catalyst for the conversion of cyclohexane to adipic acid, $Fe(CF_3SO_3)_2$ and dpphen, or $Fe(tma)_3$ and dpphen, is added separately in various stoichiometric ratios (e.g., dpphen:Fe= 2:1, 3:1, 6:1, or 12:1) to a volume of cyclohexane and, optionally, ortho-dichlorobenzene in a stainless steel autoclave reactor. After reacting the reaction mixture at a temperature to about 130° C. in the presence of oxygen (e.g., partial pressure 550 kPa or 80 psi), the reaction yields adipic acid in a much greater quantity when the catalyst is present compared to reactions where it is omitted.

Another preferred method of making a catalyst for catalyzing the synthesis of a chemical product from a hydrocarbon and oxygen includes the steps of: (A) mixing together a composition including an organic ligand (e.g., pyridyl compound) and a composition comprising a transition element to form a reaction mixture; (B) allowing the reaction mixture to react under conditions which result in the formation of a solid material comprising the catalyst; and (C) purifying the solid material from the reaction mixture. For example, to make a catalyst for the conversion of cyclohexane to adipic acid, a solution of 1 g of dpphen dissolved in 50 ml $C_2H_5OH$ is prepared and then added to 10 ml of an aqueous solution containing 0.42 g $Fe(CF_3SO_3)_2$. After stirring overnight (e.g., 8 to 16 hours), the resulting red precipitate is collected by filtration. This method results in approximately a 70% yield, with the solid compound having the apparent formula of $Fe(dpphen)_3(CF_3SO_3)_2$ as confirmed by X-ray crystallography. Mass spectrometric analysis suggested that the tris-chelate ion $[Fe(dpphen)_3]^{2+}$ is present in solutions of the compound in methanol.

Methods For Catalyzing Synthetic Reactions

The invention also features methods for catalyzing the synthesis of a chemical from a hydrocarbon and oxygen. Preferred such methods include the steps of: (A) providing a catalyst comprising a transition element and an organic ligand (e.g., a pyridyl compound); (B) mixing the catalyst with the hydrocarbon and an oxygen source to form a reaction mixture; and (C) placing the reaction mixture under conditions that result in the production of the chemical in the reaction mixture.

For example, to catalyze the conversion of cyclohexane to adipic acid, a catalyst of Fe(II), Fe(III), or Ru(II) complexed with pyridine, dpbp, phen, dpphen, or dmdpphen, is prepared as a solid by mixing a salt of Fe(II), Fe(III), or Ru(II) [e.g., $Fe(CF_3SO_3)_2$, $Fe((CH_3)_3CCO_2)_3$, or $(RuCl_2)$] dissolved in water with a solution of pyridine, dpbp, phen, dpphen, or dmdpphen dissolved in ethanol. The resulting precipitate is isolated and then added to a volume of cyclohexane and, if necessary or desired, a cosolvent such as ortho-dichlorobenzene to form the reaction mixture.

The reaction mixture is then placed in a reaction chamber (e.g., glass bottle or autoclave). The reaction chamber is then charged with oxygen (e.g., air with partial $O_2$ pressure of about 200–3500 kPa), sealed, and then heated to a temperature of between about 100–150 ° C. to initiate the reaction. The reaction is allowed to continue for a few hours (e.g., 3–6 hours), after which time the reaction mixture is cooled (e.g., by placing the reaction mixture in an ice bath) to precipitate out solid adipic acid particles. The adipic acid particles can be separated from the liquid remaining after the process by any suitable process (e.g., filtration). Many variations or adaptations of the foregoing are also within the invention as described below and in the Examples.

Reaction Type

Synthetic reactions catalyzed according to the invention can be any compatible with the catalysts of the invention. Generally, preferred reactions are those involving the oxidation of a hydrocarbon into a chemical product. The presently preferred reaction is the synthesis of adipic acid by oxidation of cyclohexane as many catalysts within the invention have been analyzed using this reaction.

Catalyst: Hydrocarbon Ratios

The amount of catalyst per amount of hydrocarbon will vary widely depending on factors such as the particular catalyst selected, the particular reaction to be catalyzed, quantity or concentration of hydrocarbon present, cosolvent, pressure, temperature, and other reaction conditions. Such catalyst:hydrocarbon ratios can be determined empirically by comparing the amount of chemical product produced using a range of different ratios. Those that produce more of the chemical product are preferred; and those that produce the most chemical product are most preferred. Generally, suitable catalyst:hydrocarbon ratios will vary from about $10^{-8}$ to about $10^{-2}$ moles of catalyst per mole of hydrocarbon.

For the catalytic oxidation of cyclohexane to adipic acid using a Ru or Fe complexed with pyridine, phen, dpphen or dpdmphen with or without an ortho-dichlorobenzene cosolvent at between 100–150° C. and 200–3500 partial pressure of $O_2$, the amount of catalyst employed can range from about $10^{-7}$ moles to about $10^{-3}$ moles per mole of cyclohexane. Preferably, however, this range is about $10^{-6}$ to $10^{-4}$ moles of catalyst per mole of cyclohexane. Other catalyst:hydrocarbon ratios are not precluded.

Reaction Conditions

Temperature

The step of placing the reaction mixture under conditions that result in the production of the chemical product in the reaction mixture typically comprises a step of adjusting the temperature of the reaction mixture to a temperature suitable for the reaction to proceed. The particular temperature or range of temperatures chosen will vary according to several parameters including the particular reaction selected, the concentration of the reactants in the reaction mixture, the pressure of the reaction mixture, etc. Such temperatures can be extrapolated from temperatures known to be optimal for reactions similar to those of the selected reaction (i.e., the conventional synthetic methods or similar methods using conventional catalysts) to get a general range of suitable temperatures. Experiments can then be performed by using a catalyst of the invention in an adaptation of the conventional methods, and the temperature can be varied around the extrapolated general range of suitable temperatures to find suitable and/or optimal temperature(s) for the processes of the invention. Generally, those temperatures at which the greatest amount of chemical product is produced are preferred. For many reactions, suitable temperatures range from about 25° C. to about 250° C., although this range can vary substantially.

For the synthesis of adipic acid from cyclohexane using an ortho-dichlorobenzenie cosolvent and an Fe(II)-dpphen, Fe(II)-dmdpphen, or Ru-dmdpphen catalyst; or using an Fe(III)-phen, Fe(III)-pyridine, or Fe(III)-dpphen catalyst without co-solvent; for initial $O_2$ partial pressures of between about 200–3500 kPa, the presently preferred temperature is between about 100–150° C. (e.g., 100° C., 105° C., 110° C., 110° C., 115° C., 120° C., 125° C., 130° C., 135° C., 140° C., 145° C., 150° C.). For example, good adipic acid production is often obtained when the temperature of the reaction mixture is maintained at about 130° C.

In addition to placing the reaction mixture at a temperature suitable for catalyzing the synthesis of a chemical product, the invention also includes a step of cooling the reaction mixture to precipitate out solid particles of the chemical product in the reaction mixture after the reaction the step. Depending on the particular reaction, the temperature at which precipitation occurs will vary; but suitable such temperatures can easily be determined by simply cooling the reacted reaction mixture until solid particles of the chemical product are observed. Temperatures below the chemical product's melting point but above the melting point of the other components of the reaction mixture arc generally preferred for this step. In the preferred synthesis of adipic acid from cyclohexane, placing the reaction mixture in an ice bath (i.e., around 0° C.) is suitable for this step.

Pressure

The step of placing the reaction mixture under conditions that result in the production of the chemical in the reaction mixture can also comprise a step of adjusting the pressure of the reaction mixture to a pressure suitable for the reaction to proceed. Because gaseous dioxygen added to the reaction mixture is both a reactant and a vehicle for producing pressure in the vessel containing the reaction mixture, the amount of oxygen added to the reaction mixture is usually a more important factor in the reaction than the overall pressure (i.e., partial pressure of $O_2$ combined with partial pressure of other included gases) to which the reaction mixture is subjected.

The particular pressure or range of pressures chosen will vary according to several parameters including the particular reaction selected, the concentration of the reactants in the reaction mixture, the temperature of the reaction mixture, the oxygen source used, etc. Such pressures can be extrapolated from pressures known to be optimal for reactions similar to those of the selected reaction (i.e., the conventional synthetic methods or similar methods using conventional catalysts) to obtain a general range of suitable pressures. Experiments can then be performed by using a catalyst of the invention in an adaptation of the conventional methods, and the pressure can be varied around the extrapolated general range of suitable pressures to find the most optimal pressure(s) for the processes of the invention. For example, those pressures at which the greatest amount of chemical product is produced might be optimal. For many reactions, suitable $O_2$ partial pressures range from about 50 kPa to about 10,000 kPa, although this range can vary substantially.

For the synthesis of adipic acid from cyclohexane using an ortho-dichlorobenzene cosolvent and an Fe(II)-dpphen, Fe(II)-dmdpphen, or Ru-dmdpphen catalyst; or using an Fe(III)-phen, Fe(II)-pyridine, or Fe(III)-dpphen catalyst without co-solvent; for temperatures between about 100–150° C., the presently preferred $O_2$ partial pressures are between about 200–3500 kPa. For example, good adipic acid production is often obtained when the partial 0 pressure of the reaction mixture is maintained at about 550 kPa. Thus, using only pure gaseous dioxygen in the reaction, a preferred pressure is about 550 kPa. In comparison, using only air as the oxygen source, the comparable pressure would be about 2750 kPa.

Other pressures are suitable for the invention. For example, one of the advantages of the invention over conventional methods for the one step air oxidation of cyclohexane to adipic acid, is that lower pressures (e.g., less than about 750 kPa) can be used such that the process can be performed using less costly equipment. For example, although the reactions may proceed slowly under reduced pressure, in come cases processes within the invention can be performed at about standard atmospheric air pressure or slightly above or below such pressure (e.g., about 60–300 kPa air pressure/ about 10–50 kPa partial $O_2$ pressure).

Duration

The duration of the reaction will depend upon the particular reaction and reaction conditions selected. Generally, the amount of time for the reaction to occur will vary from the time between (a) the initiation of the reaction and the first appearance of the chemical product and (b) the initiation of the reaction and the termination of chemical product synthesis (e.g., due to exhaustion of reagents or production of interfering by-products). Thus the reaction can last for less than a few seconds to several days or even longer. The reaction can even proceed continuously (see below). For the production of adipic acid by oxidation of cyclohexane according to several methods of the invention, the reaction generally lasts from one to several hours (see examples below).

Cosolvent

The amount of cosolvent to be added to the reaction mixture to facilitate the catalytic production of a chemical product will vary depending upon various factors including the particular cosolvent, hydrocarbon, catalyst, reaction, and reaction conditions selected. Appropriate amounts of cosolvent can be determined empirically by, for example, comparing the amount of chemical product produced upon addition of different amounts of cosolvent to the reaction mixture and then selecting the cosolvent concentrations which maximize production of the chemical product. For the production of adipic acid by oxidation of cyclohexane using an ortho-dichlorobenzene cosolvent, a reaction temperature of between 100–150° C., and partial pressure of O2 of about 550 kPa, suitable cosolvent:cyclohexane ratios (vol:vol) are about 10:90 to 90:10 (e.g., about 25:75, 35:65, 50:50, 60:40, and 80:20).

Isolation of Reaction Products

Also within the invention is a method for isolating and/or purifying a chemical product from a reacted reaction mixture. This method can be performed by any technique known for separating a mixture of different substances. For example, this method can include a step of extraction, chromatography, distillation, etc. Preferred reactions of the invention yield a chemical product that is in a different phase than the other components of the reacted reaction mixture. In the case where one is a solid and the other is a liquid, filtration is a preferred method of isolating and purifying the chemical product. For example, for the production of adipic acid by oxidation of cyclohexane as described above, after cooling the reaction mixture, solid particles of adipic acid are formed in the liquid reaction mixture. The reaction mixture can be passed through filter paper to separate the solid adipic acid from the liquid (i.e., the filtrate). If desired, the solid product can be further purified by techniques known in the art. For example, the solid particles can be washed with acetonitrile or recrystallized.

Continuous Reactions

The above described methods for synthesizing chemical products by oxidation of a hydrocarbon can be adapted to be performed continuously. Preferred such methods include the steps of: (A) providing a catalyst comprising a transition element and an organic ligand (e.g., a pyridyl compound); (B) mixing the catalyst with the hydrocarbon and an oxygen source to form a reaction mixture; and (C) placing the reaction mixture under conditions that result in the production of the chemical product in the reaction mixture; (D) separating the chemical product from the other components remaining in the reacted (or partially reacted) reaction mixture; and (E) placing the reacted reaction mixture under the conditions that result in the further production of the chemical product. Steps D and E can be performed repeatedly, or until the reaction mixture can no longer be caused to produce the chemical product (e.g., because of exhaustion of one of the reactants or the catalyst). Additionally, step E can include adding more reactant (e.g., hydrocarbon or oxygen), cosolvent, or catalyst. Addition of oxygen to the reaction can be performed using an oxygen reservoir to maintain the oxygen pressure at predetermined levels within a reaction vessel containing the reaction mixture. Step E can also include a step of removing byproducts of the reaction.

For example, for the synthesis of adipic acid by oxidation of cyclohexane as described elsewhere herein, after partially reacting the reaction mixture in a reaction vessel under conditions that yield solid adipic acid, the adipic acid is separated from the liquid portion of the partially reacted reaction mixture by filtration. The filtrate is then returned to the reaction vessel and subjected to the same or similar conditions which cause production of adipic acid.

Thereafter, the solid adipic acid is again filtered from the further reacted reaction mixture, and the filtrate is again returned to the reaction vessel for further reaction. This cycle can be repeated ad nauseain or until a necessary reactant or the catalyst is depleted. This process can be automated by, for example, adapting industrial chemical production equipment to run the synthetic reaction as a continuous process whereby adipic acid product is continually purified from the reaction mixture (e.g., by cooling a portion of the reaction mixture, collecting the solid adipic acid particles, and returning the remaining liquid to the reaction), and adding additional reactants, cosolvent, and/or catalyst to the reaction mixture as needed.

Kits

A kit for catalyzing the synthesis of a chemical product (e.g., adipic acid) from a hydrocarbon (e.g., cyclohexane) is also within the invention. The kit can include a catalyst of the invention such as a transition element complexed with a pyridyl ligand, and written instructions for using the catalyst for catalyzing the synthesis of the chemical product from the hydrocarbon. The kit may also include written information regarding the safety of the catalyst, and suitable packaging for safely transporting the catalyst.

EXAMPLES

Example I—Preparation and Analysis of a Catalyst

A solid oxidation catalyst was prepared by addition of dpphen in $C_2H_5OH$ to an aqueous solution of $Fe(CF_3SO_3)_2$. Specifically, a solution of 1 g of dpphen dissolved in 50 ml $C_2H_5OH$ was prepared and then added to 10 ml of an aqueous solution containing 0.42 g $Fe(CF_3SO_3)O_2$. After stirring overnight (e.g., 8 to 16 hours), the resulting red precipitate is collected by filtration. The recrystallized solid compound was obtained in 70% yield and had the apparent formula $Fe(dpphen)_3(CF_3SO_3)_2$ Electrospray mass spectrometric analysis showed that the tris-chelate ion $[Fe(dpphen)_3]^{2+}$ was present in solutions of the compound in methanol. X-ray crystallography confirmed that the compound was the tris-chelate complex.

Example II—Catalytic Synthesis of Adipic Acid from Cyclohexane

Several experiments were performed that demonstrate the catalytic oxidation of cyclohexane to adipic acid using various catalysts within the invention under different reaction conditions. The oxidation reactions were carried out in either (a) a 250 mL glass bottle reactor (Reactions 1–15) at 120° C. or (b) a 300 mL titanium reactor (Reactions 16–19 at the temperature indicated). Reaction vessels were pressurized with 3 atm air before heating (except for reaction 4-an oxygen enrichment experiment: 35 psi air+10 psi $O_2$). The reaction mixtures were prepared by mixing together the following: catalyst, o-dichlorobenzene (10 mL in glass; 20 mL in bomb; for reaction 15, 10 mL $CH_3CN$ was used instead of 10 mL o-dichlorobenzene), cyclohexane (5 mL in glass, 10 mL in bomb). Results of the experiments are shown below in Table 1. AA=adipic acid, K=ketone (cyclohexanoic), A=alcohol (cyclohexanol). Error limits are ±σ values from duplicate or triplicate runs. Fe-porphyrin= iron(III) tetra-(pentafluorophenyl) porphyrin chloride; Co-nap=cobalt naphthenate; dpphen=4,7-diphenyl-1,10- phenanthroline; Trf=triflate ($CF_3SO_3^-$). For reactions 6–12 and 14, the catalyst was generated in situ. Amount column indicates molds of transition metal salt.

In reaction 19, cyclohexane was oxidized to a 1:7.1:6.0 mixture of adipic acid, cyclohexanone and cyclohexanol after 5 hours (turnovers: 21 (acid), 149 (ketone), 126 (alcohol); ~6 % total conversion). The crude adipic acid product was collected by filtration after cooling the reaction mixture. Analyses of the isolated adipic acid were performed using elemental analysis, mass spectrometry, infrared spectroscopy, and $^1H/^{13}C$ NMR with comparisons to an authentic adipic acid sample. All analytical results showed that the isolated adipic acid (crude, washed with o-dichlorobenzene, but not recrystallized) was >95 % pure. NMR analysis showed that glutaric acid was also produced (<5 %) along with much lower amounts of shorter chain acids such as formic acid, butyric acid, valeric acid, etc. Only trace amounts of ketone and alcohol (and no adipic acid) were observed when the catalyst is omitted or replaced with 3 equivalents of dpphen alone.

As shown by the results of reactions 16–19, the catalytic oxidation was sensitive to reaction temperature, as product yields increased with increasing temperature up to 140° C. Time dependence data down to a reaction time of 1.0 h (not shown) showed that there was no induction period for the reaction. Higher yields of adipic acid were also obtained by partial replacement of air by $O_2$ (reaction 4). Stoichiometry was assessed by comparison of $O_2$ consumed to the total oxidized hydrocarbon products and $CO_2/CO$ yield (<10% of converted cyclohexane from GC analysis of the vapor phase over the reaction solution). The observed $O_2$ consumption was consistent with the production of cyclohexanol, cyclohexanone, adipic acid, glutaric acid, water and $CO_2/CO$ as the only major products.

The chloride and perchlorate salts of $[Fe(dpphen)_3]^{2+}$ had roughly the same activity as the triflate salt (reactions 5 and 6). $[Fe(phen)_3]Cl_2$ and $[Fe(phen)_3](CF_3SO_3)_2$ were inactive for production of adipic acid, as were cobalt(III) acetate and cobalt naphthenate (reactions 13 and 15).

When the reaction was performed under the same conditions as above except that the catalyst components (Fe $(CF_3SO_3)_2$ and dpphen) were prepared in situ by adding to the reaction mixture separately in various stoichiometric ratios (reactions 7–10), adipic acid production was comparable at dpphen:Fe ratios of 2:1, 3:1, or 6:1 and is essentially the same as that found for the solid catalyst $[Fe(dpphen)_3](CF_3SO_3)_2$. The analogous ruthenium complex, $[Ru(dpphen)_3]Cl_2$ was found to be inactive for all products despite good solubility (reaction 11). In other experiments (not shown) under similar reaction conditions, $Ru(dmdpphen)_2Cl_2$ was able to catalyze the production of adipic acid by oxidation of cyclohexane.

TABLE 1

Catalytic autoxidation of cyclohexane with various catalysts.

| Reaction | Catalyst[b] | Amount/ $10^{-5}$ mol | AA/$10^{-4}$ mol | K/$10^{-4}$ mol | A/$10^{-4}$ mol | Time/hours |
|---|---|---|---|---|---|---|
| 1 | $[Fe(dpphen)_3](Trf)_2$ | 0.88 | 2.5 ± 0.5 | 7.1 ± 1.3 | 4.3 ± 1.3 | 6 |
| 2 | $[Fe(dpphen)_3](Trf)_2$ | 0.88 | 2.6 | 8.9 | 7.6 | 4 |
| 3 | $[Fe(dpphen)_3](Trf)_2$ | 0.88 | 1.6 | 6.6 | 5.2 | 2 |
| 4 | $[Fe(dpphen)_3](Trf)_2$[f] | 0.88 | 3.6 | 10.4 | 6.3 | 6 |
| 5 | $[Fe(dpphen)_3](ClO_4)_2$ | 0.88 | 2.7 | 8.4 | 3.3 | 6 |
| 6 | $[Fe(dpphen)_3]Cl_2$[e] | 0.88 | 2.4 | 10.1 | 6.6 | 6 |

TABLE 1-continued

Catalytic autoxidation of cyclohexane with various catalysts.

| Reaction | Catalyst[b] | Amount/ $10^{-5}$ mol | AA/$10^{-4}$ mol | K/$10^{-4}$ mol | A/$10^{-4}$ mol | Time/hours |
|---|---|---|---|---|---|---|
| 7  | 1:1 dpphen:Fe(Trf)$_2$[c] | 0.88 | 0.4 ± 0.2 | 2.4 ± 0.9 | 2.8 ± 0.7 | 6 |
| 8  | 2:1 dpphen:Fe(Trf)$_2$[c] | 0.88 | 1.8 ± 0.4 | 7.1 ± 0.7 | 6 ± 2 | 6 |
| 9  | 3:1 dpphen:Fe(Trf)$_2$[c] | 0.88 | 1.5 ± 0.4 | 8.3 ± 1.3 | 4.7 ± 1.8 | 6 |
| 10 | 6:1 dpphen:Fe(Trf)$_2$[c] | 0.88 | 2.3 ± 0.4 | 9.9 ± 1.9 | 4 ± 2 | 6 |
| 11 | [Ru(dpphen)$_3$]Cl$_2$[e] | 0.88 | 0 | 0 | 0 | 6 |
| 12 | Mn(dpphen)$_2$Cl$_2$[c] | 0.88 | trace | trace | trace | 20 |
| 13 | Co(CH$_3$COO)$_2$ | 8.8 | 0 | 0.94 | trace | 6 |
| 14 | Fe-porphyrin[c] | 0.88 | 0 | 11.6 | 2.9 | 3 |
| 15 | Co-nap[d] | 0.88 | 0 | 8.9 | — | 6 |
| 16 | [Fe(dpphen)$_3$](Trf)$_2$ (110° C.)[g] | 1.76 | 0.01 | 4.4 | 4.7 | 5 |
| 17 | [Fe(dpphen)$_3$](Trf)$_2$ (120° C.)[g] | 1.76 | 1.6 | 10.6 | 9.3 | 5 |
| 18 | [Fe(dpphen)$_3$](Trf)$_2$ (130° C.)[g] | 1.76 | 2.7 | 18.3 | 13.8 | 5 |
| 19 | [Fe(dpphen)$_3$](Trf)$_2$ (140° C.)[g] | 1.76 | 3.7 | 26.3 | 22.1 | 5 |

In another experiment, consumption of oxygen by the reaction was measured. 100 ml cyclohexane (0.92 mol), 45 mg of Fe(dpphen)$_3$(Trf)$_2$ (3×10mol) were combined in a 0.30 L Parr Pressure reactor, initial p(O$_2$)=50 psi. Upon heating to 132±3° C. pressure rose to 100 psi and slowly decreased to 86 psi and the pressure was maintained by using the gas burette to replenish the consumed O$_2$. Oxygen uptake typically stopped after loss of ~70–80 psi in the burette. The reaction was repeated for four runs (a run= allowing the reaction to proceed until no more than 0. 10 mol of oxygen is consumed, cooling the solution, filtering out the produced adipic acid, and returning the filtrate to the reactor, and repeating the reaction). Reaction rates for each of the runs were: 720 mol O$_2$/mol Fe hr for run 1; 1000 mol O$_2$/mol Fe hr for run 2; 1350 mol O$_2$/mol Fe hr for run 3; and 1220 mol O2/ mol Fe hr for run 4. A total of 0.025 mol of adipic acid was produced.

Example III—Effect of Additives

The effect of various additives on a preferred process of cyclohexane oxidation was examined. 5 ml of cyclohexane, 10 ml of ortho-dichlorobenzene, and 0.88×10$^{-6}$ mol Fe(dpphen)$_3$(CF$_3$SO$_3$)$_2$ and various additives were mixed together in a 250 ml glass reactor heated by an oil bath. The reactor was charged with 3 atmospheres of air and then heated to 120° C. After 6 hours the contents of the reactor was analyzed.

The results obtained indicated that adding a small amount of H$_2$O had no effect on the reactivity of the catalyst and the product distribution. The reaction was also tolerant of at least small amounts of acid but suffered with small amounts of base. Cyclohexylhydroperoxide (CHP) was thought to be a possible intermediate formed in cyclohexane oxidation. Adding CHP to the reaction system significantly enhanced the yield of adipic acid. Additionally, the amount of cyclohexanone and cyclohexanol produced were relatively unchanged. However, only cyclohexanone and cyclohexanol were formed while using CHP alone without catalyst, and the products can be attributed to the decomposition products of CHP.

Example IV—Regeneration of Reaction Products

A reaction mixture was prepared by combining together 0.05 L cyclohexane (0.46 mol), 0.05 L o-dichlorobenzene, and 45 mg Fe(dpphen)$_3$(Trf)$_2$(3×10$^{-5}$ mol) in a 0.30 steel autoclave reactor equipped with a mechanical stirrer, gas entrainment impeller, thermocouple, and a temperature control device. The reactor was charged with 50 psi O$_2$, and the reaction mixture contained therein was heated to 132±3° C. After reaching 132±3° C., the O$_2$ pressure in the reactor was 80 psi and this pressure was maintained by using a gas burette to replenish the consumed oxygen. Consumption of oxygen was monitored with a separate gauge on the burette. The reactions were allowed to continue until no more than 0.12 mol of O$_2$ was consumed (about 3–5 hrs). The reactor was then cooled in an ice bath and depressurized. Solid adipic acid was then collected from the reacted reaction mixture by filtration.

After completing a reaction as described above, the filtrate solution (i.e., the liquid portion of the reacted reaction mixture remaining after the solid adipic acid was removed) was returned to the reactor and additional cyclohexane and solvent was added. This reaction procedure described above was then repeated to produce additional adipic acid. This process was repeated for four runs. As shown in Table 2, adipic acid continued to be produced even after the fourth run. (Reference to EX means X 10$^x$).

TABLE 2

| Run # | 1 | 2 | 3 | 4 |
|---|---|---|---|---|
| Starting materials: added | | | | |
| Catalyst (mol) | 3.00E-05 | 0 | 0 | 0 |
| Cyclohexane (ml) | 50 | 5 | 5 | 5 |
| O-dichlorobenzene (ml) | 50 | 5 | 5 | 10 |
| Filtrate from Prior Run (ml) | 0 | 90 | 90 | 85 |
| Reaction conditions: | | | | |
| Temperature | 132 ± 3 | 132 ± 3 | 132 ± 3 | 132 ± 3 |
| O2 pressure (room temp.) | 50 | 50 | 50 | 50 |

TABLE 2-continued

| Run # | 1 | 2 | 3 | 4 |
|---|---|---|---|---|
| Time (hr) | 3 | 4.5 | 4 | 3.5 |
| Results: | | | | |
| Products | | | | |
| Cyclohexanone (mol) | 1.72E-02 | 2.40E-02 | 2.35E-02 | 2.54E-02 |
| Cyclohexanol (mol) | 1.50E-02 | 1.50E-02 | 1.25E-02 | 1.15E-02 |
| Adipic Acid (mol) | 4.40E-03 | 1.04E-02 | 1.05E-02 | 8.80E-03 |

This experiment was repeated as above using $Fe(dmdpphen)_2TrF_2$ as the catalyst instead of $Fe(dpphen)_3TrF_2$. Adipic acid also continued to be produced using this catalyst even after a fourth run (data not shown).

$Fe(tma)_3$-based catalysts were also active in catalyzing oxidation of cyclohexane to adipic acid. $Fe(tma)_3$ was made by dissolving 1.20 g of anhydrous $FeCl_3$ (0.022 mol) in 15 ml of $H_2O$ in a first flask. A second flask was charged with 0.88 g of NaOH (0.022 mol), 2.27 g of trimethylacetic acid and 20 ml of $H_2O$. The two solutions were mixed together and a peach colored precipitate appeared. The solution was allowed to stir for one hour and then filtered to yield $Fe(tma)_3$ as a peach colored solid. A reaction mixture was prepared by combining together 100 ml cyclohexane (0.46 mol), $3.5 \times 10^{-5}$ mol $Fe(tma)_3$, and $10.5 \times 10^{-5}$ mol (0.035 g) dpphen in a 0.30 L stainless steel autoclave reactor equipped with a mechanical stirrer, gas entrainment impeller, thermocouple, and a temperature control device. The reactor was charged with 50 psi $O_2$, and the reaction mixture contained therein was heated to 133±3° C. After reaching 133±3° C., the $O_2$ pressure in the reactor was 100 psi and this pressure was maintained by using a gas burette to replenish the consumed oxygen. Consumption of oxygen was monitored with a separate gauge on the burette. A total of two runs (a run=allowing the reaction to proceed until no more than 0.10 mol of oxygen is consumed, cooling the solution, filtering out the produced adipic acid, and returning the filtrate to the reactor, and repeating the reaction) were performed, and a total of 2.0 grams of adipic acid was obtained.

The foregoing experiment was repeated using 1,10-phenanthroline in place of dpphen. A reaction mixture was prepared by combining together 100 ml cyclohexane, $4.18 \times 1^{-5}$ mol $Fe(tma)_3$, and $12.5 \times 10^5$ mol 1,10-phenanthroline in a 0.30 L stainless steel autoclave reactor, and the reaction was carried out as described above. The reaction was carried out for 4 runs yielding 3.88 grams of adipic acid. This experiment was again repeated using pyridine rather than dpphen or 1,10-phenanthroline. In this experiment, a reaction mixture was prepared by combining together 100 ml cyclohexane, $3.9 \times 10^{-5}$ mol $Fe(tma)_3$, and $2.45 \times 10^-$mol pyridine in a 0.30 L stainless steel autoclave reactor. The reactor was charged with an initial p ($O_2$)=50 psi. Upon heating to 133±3° C., the pressure in the reactor rose to 100 psi and slowly decreased to 86 psi. This pressure was maintained by using a gas burette to replenish the consumed oxygen. Consumption of oxygen was monitored with a separate gauge on the burette. The reactions were allowed to continue until no more than 0.10 mol of $O_2$ was consumed (2–8 hrs). The reactor was then cooled in an ice bath and depressurized. Reaction solution was filtered to remove the solid adipic acid, and the soluble products were monitored by gas chromatographic analysis. Initially the $Fe(tma)_3$ generated an orange solution when dissolved into the cyclohexane. After the reaction was complete (about 0.08 mol of $O_2$ consumed) and the formed adipic acid removed, the solution was light yellow and homogeneous. This yellow solution was returned to the autoclave reactor and reaction was repeated. This process was repeated. Results are shown below in Table 3. After 3 runs, a total of 3.33 g of adipic acid was obtained. In another experiment, under reaction identical conditions, except using $3.8 \times 10^{-5}$ mol $Fe(tma)_3$ and $4.65 \times 10^{-4}$ mol pyridine dissolved in 100 ml cyclohexane, a total of 9.6 grams adipic acid was obtained after 7 runs. Results from the first 5 runs are shown below in Table 4.

TABLE 3

| Run # | 1 | 2 | 3 |
|---|---|---|---|
| Starting materials: added | | | |
| Fe(tma)₃ (mol) | 3.90E-05 | 0 | 0 |
| Pyridine (mol) | 2.45E-04 | 0 | 0 |
| Cyclohexane (ml) | 100 | 10 | 8 |
| Filtrate from run 1 | 0 | 90 | 92 |
| Reaction conditions: | | | |
| Temperature | 133 ± 3 | 133 ± 3 | 133 ± 3 |
| O2 pressure (maintained) | 50 | 50 | 50 |
| Time (hr) | 8 | 3.3 | 2.5 |
| Rate (mol O₂/hr mol Fe) | 150 | 950 | 1200 |
| Results: | | | |
| Adipic Acid (mol) | 3.60E-03 | 6.15E-03 | 1.30E-02 |
| % conversion (Cy to AA) | 0.40 | 0.70 | 1.41 |

TABLE 4

| Run # | 1 | 2 | 3 | 4 | 5 |
|---|---|---|---|---|---|
| Starting materials: added | | | | | |
| Fe(tma)₃ (mol) | 3.90E-05 | 0 | 0 | 0 | 0 |
| Pyridine (mol) | 4.90E-04 | 0 | 0 | 0 | 0 |
| Cyclohexane (ml) | 100 | 8 | 10 | 11 | 11 |
| Filtrate from run 1 | 0 | 92 | 90 | 89 | 89 |
| Reaction conditions: | | | | | |
| Temperature | 133 ± 3 | 133 ± 3 | 133 ± 3 | 133 ± 3 | 133 ± 3 |
| O2 pressure (maintained) | 50 | 50 | 50 | 50 | 50 |
| Time (hr) | 6.8 | 3.5 | 2.33 | 2.5 | 2.33 |
| Rate (mol O₂/hr mol Fe) | 450 | 825 | 975 | 1200 | 1060 |
| Results: | | | | | |
| Adipic Acid (mol) | 3.90E-03 | 9.60E-03 | 7.50E-03 | 1.57E-02 | 1.10E-02 |
| % conversion (Cy to AA) | 0.42 | 1.04 | .82 | 1.7 | 1.2 |

Example V—Oxidation of Cyclohexane To Adipic Acid Using Catalysts

A reaction mixture was prepared by combining together 50 ml cyclohexane (0.46 mol), 50 ml dichlorobenzene, 0.023g ($5.4 \times 10^{-5}$ mol) of $Fe(Trf)_2$ and 0.054 g ($1.6 \times 10^{-4}$ mol) of dpphen in a 0.30 L stainless steel autoclave reactor equipped with a mechanical stirrer, gas entrainment impeller, thermocouple, and a temperature control device. The reactor was charged with and 250 psi of air (p $O_2$=50 psi), and the reaction mixture contained therein was heated to 135° C. for 6 hours. It was then cooled in an ice bath and depressurized. Reaction solution was filtered to remove the solid adipic acid. This procedure was also performed using $Ru(dmdpphen)_2Cl_2$ as the catalyst. Using either catalyst, solid adipic acid was collected from the reacted reaction mixture by filtration. In experiments using preformed iron (II) complexed with ligands similar to 4,7-diphenyl-1,10-phenanthroline as a catalyst, it was found that bidentate ligands that have the same diphenyl functionality as dpphen (e.g., 4,4'-diphenyl-2,2'-bipryidine and 2,9-dimethyl-4,7-diphenyl-1,10-phenanthroline) are active.

Example VI—Solvent Dependence

Solvent variation experiments were undertaken to determine the optimal ratios of cyclohexane: dichlorobenzene (vol:vol) for catalyzing the synthesis of adipic acid by cyclohexane oxidation. A reaction mixture was prepared by combining together 0.05 L cyclohexane (0.46 mol), o-dichlorobenzene (volume adjusted per the ratios listed below), and 45 mg Fe(dpphen)$_3$(CF$_3$SO$_3$)$_2$ ($3\times10^{-5}$ mol) in a 0.30 L stainless steel autoclave reactor equipped with a mechanical stirrer, gas entrainment impeller, thermocouple, and a temperature control device. The reactor was charged with 250 psi air, and the reaction mixture contained therein was heated to 132±3° C. The reaction was run until pressure in the reactors ceased to change (about 3–5 hours). Thereafter, the reaction mixtures were cooled in an ice bath and the precipitates containing solid adipic acid were collected by filtration. Hydrocarbon:solvent ratios of 25:75, 35:65, 50:50, 60:40, and 80:20 each resulted in measurable production of adipic acid. Adipic acid production was maximized at the 50:50 ratio.

The effect of solvent variation was also investigated in another experiment. A reaction mixture was prepared by combining together 100 ml of cyclohexane and /or o-dichlorobenzene solution, $3\times10^{-5}$ mol Fe(dpphen)$_3$ (CF$_3$SO$_3$)$_2$ ($3\times10^{-5}$ mol) in a 0.30 L stainless steel autoclave reactor equipped with a mechanical stirrer, gas entrainment impeller, thermocouple, and a temperature control device. Six cyclohexane/dichlorobenzene mixtures were tested: (1) 90 ml of dichlorobenzene and 10 ml cyclohexane; (2) 50 ml of dichlorobenzene and 50 ml cyclohexane; (3) 30 ml of dichlorobenzene and 70 ml cyclohexane, (4) 10 ml of dichlorobenzene and 90 ml cyclohexane; (5) 5 ml of dichlorobenzene, 95 ml cyclohexane; and (6) no dichlorobenzene and 100 ml cyclohexane. The reactor was charged with 250 psi air, and the reaction mixture contained therein was heated to 132±3° C. The reaction was run until pressure in the reactors ceased to change (about 3–5 hours). Thereafter, the reaction mixtures were cooled in an ice bath and the precipitates containing solid adipic acid were collected by filtration. Mixture (1) resulted in the production of: $1.0\times10^{-3}$ mol adipic acid, and only trace quantities of cyclohexanone (one) and cyclohexanol (ol). Mixture (2) resulted in the production of: $1.5\times10^{-2}$ mol adipic acid, $3.12\times10^{-2}$ mol one, and $1.2\times10^{-2}$ mol ol. Mixture (3) resulted in the production of: $1.4\times10^{-2}$ mol adipic acid, $3.18\times10^{-2}$ mol one, and $2.18\times10^{-2}$ mol ol. Mixture (4) resulted in the production of: $1.3\times10^{-2}$ mol adipic acid, $3.36\times10^{-2}$ mol one, and $2.62\times10^{-2}$ mol ol. Mixture (5) resulted in the production of: $1.3\times10^{-2}$ mol adipic acid, $3.58\times10^{-2}$ mol one, and $2.93\times10^{-2}$ mol ol. And Mixture (6) resulted in the production of: $1.1\times10^{-2}$ mol adipic acid, $2.87\times10^{-2}$ mol one, and $2.19\times10^{-2}$ mol ol.

Other Embodiments

While the above specification contains many specifics, these should not be construed as limitations on the scope of the invention, but rather as examples of preferred embodiments thereof. Many other variations are possible. Accordingly, the scope of the invention should be determined not by the embodiments illustrated, but by the appended claims and their legal equivalents.

What is claimed is:

1. A catalyst comprising a transition element complexed with a pyridyl ligand, the catalyst having the ability to catalyze the synthesis of a chemical product from a hydrocarbon and oxygen, wherein the chemical product is adipic acid and the hydrocarbon is cyclohexane.

2. The catalyst of claim 1, wherein the pyridyl ligand is selected from the group consisting of pyridine; 4,4'-diphenyl-2,2'-bipyridine; 1,10 -phenantlhroline; 4,7-diphenyl-1,110-phenanthroline; and 2,9-dimethyl-4,7-diphenyl-1,10-phenanthroline.

3. The catalyst of claim 1, wherein the transition element is iron.

4. The catalyst of claim 1, wherein the transition element is ruthenium.

5. The catalyst of claim 3, wherein the catalyst consists essentially of Fe(II) complexed with a ligand selected from the group consisting of 4,7-diphenyl-1,10-phenanthroline and 2,9-dimethyl-4,7-diphenyl-1,10-phenanthroline.

6. The catalyst of claim 3, wherein the catalyst consists essentially of Fe(III) complexed with a ligand selected from the group consisting of pyridine; 1,10 -phenanthroline; and 4,7-diphenyl-1,10-phenanthroline.

7. The catalyst of claim 4, wherein the catalyst consists essentially of Ru(II) complexed with 2,9-dimethyl-4,7-diphenyl-1,10-phenanthroline.

8. The catalyst of claim 1, wherein the transition element is complexed with a counter ion selected from the group consisting of $ClO_4^-$, $Cl^-$, $(CH_3)_3CCO_2^-$, and $CF_3SO_3^-$.

9. The catalyst of claim 1, wherein the catalyst has between one and twelve mole equivalents of the pyridyl ligand per mole equivalent of the transition element.

10. The catalyst of claim 1, wherein the catalyst has the ability to catalyze the production of adipic acid from cyclohexane in a single step process.

11. The catalyst of claim 1, wherein the catalyst has the ability to catalyze the production of adipic acid from cyclohexane without causing the production of a nitrogen oxide.

12. The catalyst of claim 1, wherein the catalyst has the ability to catalyze the production of adipic acid from cyclohexane at a concentration of about 0.00002 to about 0.002 moles of the catalyst per mole of cyclohexane.

13. The catalyst of claim 1, wherein the catalyst has the ability to catalyze the production of a solid product comprising adipic acid from cyclohexane and oxygen in a single reaction vessel, the solid product being greater than about 70% pure adipic acid.

14. The catalyst of claim 13, wherein the solid product is greater than about 95% pure adipic acid.

15. A method of making a catalyst for the synthesis of a adipic acid from cyclohexane and oxygen, the method including the steps of:

(A) providing a transition element, a pyridyl compound, and a reaction mixture comprising the cyclohexane;

(B) adding the transition element to the reaction mixture;

(C) adding the pyridyl ligand to the reaction mixture; and (D) placing the reaction mixture under conditions which cause the transition element and pyridyl compound to be able to function together as a catalyst for the synthesis of adipic acid from cyclohexane and oxygen.

16. The method of claim 15, wherein the transition element is Fe(II) and the pyridyl compound is selected from the group consisting of 4,7-diphenyl-1,10-phenanthroline and 2,9-dimethyl-4,7-diphenyl-1,10-phenanthroline.

17. The catalyst of claim 15, wherein the transition element is Fe(III) and the pyridyl compound is selected from the group consisting of pyridine; 1,10 -phenanthroline; and 4,7-diphenyl-1,10-phenanthroline.

18. The catalyst of claim 15, wherein the transition element is Ru(II) and the pyridyl compound is 2,9-dimethyl-4,7-diphenyl-1,10-phenanthroline.

19. A method of making a catalyst for catalyzing the synthesis of adipic acid from cyclohexane and oxygen, the method including the steps of:
(A) mixing together a composition comprising a pyridyl compound and a composition comprising a transition element to form a reaction mixture;
(B) allowing the reaction mixture to react under conditions which result in the formation of a solid material comprising the catalyst; and
(C) purifying, the solid material from the reaction mixture.

20. The method of claim 19, wherein the transition element is selected from the group consisting of: iron and ruthenium.

21. The method of claim 20, wherein the pyridyl compound is selected from the group consisting of: pyridine; 4,4'-diphenyl-2,2'-bipyridine; 1,10-phenanthroline; 4,7-diphenyl-1,10-phenanthroline; and 2,9-dimethyl-4,7-diphenyl-1,10-phenanthroline.

22. A method of catalyzing the synthesis of adipic acid from cyclohexane and oxygen, the method comprising the steps of:
(A) providing a catalyst comprising a transition element and a pyridyl compound;
(B) mixing the catalyst with the cyclohexane and the oxygen to form a reaction mixture; and
(C) placing the reaction mixture under conditions that result in the production of the adipic acid in the reaction mixture.

23. The method of claim 22, wherein the transition element is Fe(II) and the pyridyl compound is selected from the group consisting of 4,7-diphenyl-1,10-phenanthroline and 2,9-dimethyl-4,7-diphenyl-1,10-phenanthroline.

24. The method of claim 22, wherein the transition element is Fe(III) and the pyridyl compound is selected from the group consisting of pyridine; 1,10 -phenanthroline; and 4,7-diphenyl-1,10-phenanthroline.

25. The method of claim 22, wherein the transition element is Ru(II) and the pyridyl compound is 2,9-dimethyl-4,7-diphenyl-1,10-phenanthroline.

26. The method of claim 22, wherein the step of placing the reaction mixture under conditions that result in the production of the adipic acid in the reaction mixture includes placing the reaction mixture into a reaction vessel.

27. The method of claim 22, wherein the step of placing the reaction mixture under conditions that result in the production of the adipic acid in the reaction mixture comprises a step of adjusting the temperature of the reaction mixture to between about 100–150° C.

28. The method of claim 22, wherein the step of placing the reaction mixture under conditions that result in the production of the adipic acid in the reaction mixture further comprises a step of cooling the reaction mixture until a solid precipitate forms in the reaction mixture after the step of adjusting the temperature of the reaction mixture to between about 100–150° C.

29. The method of claim 22, wherein the step of placing the reaction mixture under conditions that result in the production of the adipic acid in the reaction mixture further comprises a step of adjusting the pressure of the oxygen in the reaction vessel such that the partial pressure of oxygen in the reaction vessel is between about 200 and 3500 kPa.

30. The method of claim 29, wherein the partial pressure of the oxygen in the reaction vessel is less than about 750 kPa.

31. The method of claim 22, wherein an aprotic, polar, aromatic solvent is added to the reaction mixture.

32. The method of claim 31, wherein the solvent is ortho-dichlorobenzene.

33. The method of claim 22, wherein the reaction mixture contains less than 10% by volume of an aprotic, polar, aromatic solvent.

34. The method of claim 22, wherein the adipic acid is produced as a solid precipitate in the reaction mixture.

35. The method of claim 34, further comprising the step of separating the solid precipitate from the reaction mixture to yield (a) isolated adipic acid and (b) a partially reacted reaction mixture.

36. The method of claim 35, wherein the partially reacted reaction mixture is placed into a reaction container and further reacted under conditions that result in the production of additional adipic acid.

37. The method of claim 36, wherein cyclohexane is added to the partially reacted reaction mixture, and oxygen is added to the reaction container.

38. A kit for catalyzing the synthesis of adipic acid from cyclohexane and oxygen, the kit comprising:
a catalyst comprising a transition element complexed with a pyridyl ligand, the transition element being selected from the group consisting of iron and ruthenium; and
written instructions for using the catalyst for catalyzing the synthesis of adipic acid from cyclohexane and oxygen.

39. A reaction mixture comprising cyclohexane, oxygen, and a catalyst, the catalyst comprising a transition element complexed with a pyridyl ligand, the catalyst having the ability to catalyze the synthesis of adipic acid from the cyclohexane and the oxygen.

40. The reaction mixture of claim 39, wherein the transition element is selected from the group consisting of iron and ruthenium.

41. The reaction mixture of claim 40, wherein the transition element is Fe(II) and the pyridyl compound is selected from the group consisting of 4,7-diphenyl-1,10-phenanthroline and 2,9-dimethyl-4,7-diphenyl-1,10-phenanthroline.

42. The reaction mixture of claim 40, wherein the transition element is Fe(III) and the pyridyl compound is selected from the group consisting of pyridine; 1,10 -phenanthroline; and 4,7-diphenyl-1,10-phenanthroline.

43. The reaction mixture of claim 40, wherein the transition element is Ru(II) and the pyridyl compound is 2,9-dimethyl-4,7-diphenyl-1,10-phenanthroline.

44. The reaction mixture of claim 40, wherein the catalyst consists of Fe(II) complexed with three 4,7-diphenyl-1,10-phenanthrolines.

45. The catalyst of claim 1, wherein the pyridyl ligand is not complexed with a halogen.

46. The catalyst of claim 2, wherein the pyridyl ligand is not complexed with a halogen.

47. The catalyst of claim 3, wherein the pyridyl ligand is not complexed with a halogen.

* * * * *

UNITED STATES PATENT AND TRADEMARK OFFICE
CERTIFICATE OF CORRECTION

PATENT NO.   : 6,307,100 B1
DATED        : October 23, 2001
INVENTOR(S)  : Richardson et al.

It is certified that error appears in the above-identified patent and that said Letters Patent is hereby corrected as shown below:

Column 4,
Line 26, replace "singing" with -- single --,

Column 6,
Line 63, replace "tiiflate" with -- triflate --,
Line 65, replace "clement" with -- element --, Column 11,
Line 20, replace "(II)" with -- (III) --,
Line 24, replace "0" with -- $O_2$ --, Column 13,
Line 51, replace "(cyclohexanoic)" with -- (cyclohexanone) --, Column 14,
Line 39, replace "(HII)" with -- (III) --, Column 16,
Line 24, insert -- L -- after "0.30", Column 17,
Line 46, replace "$1^{-5}$" with -- $10^{-5}$ --,
Line 46, replace "$10^5$" with -- $10^{-5}$ --,
Line 53, replace "$10^-$" with -- $10^{-4}$ --, Column 20,
Line 9, replace "-phenantlhroline" with -- phenanthroline --,
Line 10, replace "1,110" with -- 1,10 --,

UNITED STATES PATENT AND TRADEMARK OFFICE
CERTIFICATE OF CORRECTION

PATENT NO.    : 6,307,100 B1
DATED         : October 23, 2001
INVENTOR(S)   : Richardson et al.

It is certified that error appears in the above-identified patent and that said Letters Patent is hereby corrected as shown below:

Column 21,
Line 13, replace "purifying," with -- purifying --.

Signed and Sealed this

Twenty-seventh Day of August, 2002

Attest:

Attesting Officer

JAMES E. ROGAN
Director of the United States Patent and Trademark Office